United States Patent [19]

Aldwin et al.

[11] Patent Number: 5,663,306
[45] Date of Patent: Sep. 2, 1997

[54] METHOD OF CONJUGATING AN ACTIVATED ESTER TO AN AMINE-CONTAINING BIOLOGICAL MATERIAL

[75] Inventors: Lois Aldwin, San Mateo; Danute E. Nitecki, Berkeley, both of Calif.

[73] Assignee: Chiron Corporation, Emeryville, Calif.

[21] Appl. No.: 95,396

[22] Filed: Sep. 10, 1987

Related U.S. Application Data

[63] Continuation-in-part of Ser. No. 637,904, Aug. 9, 1984, abandoned.

[51] Int. Cl.$^6$ .................... C07K 1/10; A61K 39/44; G01N 33/547
[52] U.S. Cl. .................. 530/402; 424/179.1; 424/181.1; 424/183.1; 435/174; 435/177; 435/181; 436/518; 436/519; 436/532; 530/807; 530/810; 530/816; 530/403
[58] Field of Search ...................... 435/174, 177, 435/4.5, 188, 181; 560/13, 14; 260/505 R; 530/402, 403, 404, 816, 807, 810; 436/519, 827, 161, 166, 86, 87, 518, 532; 546/294; 548/546, 545; 424/179.11, 181.1, 183.1

[56] References Cited

U.S. PATENT DOCUMENTS

| | | |
|---|---|---|
| 4,253,844 | 3/1981 | Limet et al. ............... 435/177 X |
| 4,487,715 | 12/1984 | Nitecki et al. .............. 530/342 X |
| 4,517,303 | 5/1985 | Freytay et al. .............. 435/518 X |
| 4,943,636 | 7/1990 | Nitecki et al. .................. 546/294 |
| 4,954,637 | 9/1990 | Nitecki et al. .................. 548/546 |

OTHER PUBLICATIONS

Bhatnagar, et al., Peptides–Synthesis–Structure–Function, Pierce Chemical Co., Rockford, Ill. 1981, pp. 97–100.
Bodanszky, et al., J. Org. Chem., vol. 38, No. 7, 1973, pp. 1296–1300.
Klausner, et al., Peptides, John Wiley & Sons, N.Y., 1977, pp. 536–538.
Carlsson et al., Biochem. J., vol. 173, 1978, pp. 723–737.

Primary Examiner—David M. Naff
Attorney, Agent, or Firm—Dean Nakamura; Grant D. Green; Robert P. Blackburn

[57] ABSTRACT

A coupling agent which is an activated ester such as N-maleimido-6-aminocaproyl-HNSA (mal-sac-HNSA) is formed by reacting 4-hydroxyl-3-nitrobenzene sulfonic acid sodium salt (HNSA) with a carboxylic acid moiety of a compound such as N-maleimido-6-aminocaproic acid. The coupling agent is reacted with an amino group of an amine-containing biological material such as a protein at a pH of about 5.5 to 10.0 and HNSA is released. The released HNSA is spectroscopically measured at a wavelength of from about 350 nm to about 500 nm to precisely monitor and control conjugating of the coupling agent to the biological material. The resulting product is coupled to a sulfhydryl group or other group of another material to provide cross-linking between the two. This enables joining the biological material to one another, to a support matrix, to a label, to a hapten, and to other materials. An immunotoxin for therapeutic use can be prepared by conjugating the coupling agent to an antibody such as a monoclonal antibody with tumor cell specificity and then joining the resultant conjugate to a cytotoxic molecule.

11 Claims, 4 Drawing Sheets

METHOD OF CONJUGATING AN ACTIVATED ESTER TO AN AMINE-CONTAINING BIOLOGICAL MATERIAL

CROSS-REFERENCE TO RELATED APPLICATION

This application is a continuation-in-part of U.S. application Ser. No. 637,904, filed 9 Aug. 1984 now abandoned.

BACKGROUND OF THE INVENTION

1. Field of the Invention

This invention relates to a family of water-soluble esters and to their use as coupling agents. As coupling agents, the esters react with amine functionalities and thus can couple to biological materials which contain amine groups such as amine-containing proteins, polypeptides, peptides and the like. The coupling agents include a range of reagent moieties including labels and functionalities capable of entering into additional coupling reactions so as to join the amine-containing materials to one another and also to link these materials to supports as matrices, to labels, to haptens or to the like. The coupling process has the special advantage that it gives rise to a very easily monitored leaving group so that the degree of reaction is precisely monitorable and thus precisely controllable and also imparts a pronounced water solubility to the coupling agents.

2. Description of Related Disclosures

In the field of biochemistry it is often useful to cross-link species or to couple different species together so as to alter or improve their properties. For example, although short peptides generally function poorly as immunogens, a vigorous immune response may be elicited by coupling these peptides to protein carriers. Also by way of example, in general, haptens (antigens), biotin, drug derivatives or peptides may be covalently bonded to proteins or natural or synthetic polypeptides for use as immunogens or recognition tags, or to enzymes for use in homogeneous enzyme immunoassays or to other label moieties for use in specific binding assays. Similarly, antibodies may be coupled to toxins for use as immunotoxins, or to enzymes for use in enzyme immunoassays. Such cross-couplings of two generally polyfunctional molecules at defined reaction loci present a considerable challenge.

In these coupling reactions, it is often extremely important to be able to monitor the extent of coupling so as to be able to control it. Some cases, such as conjugating enzymes to antibodies, demand a one-to-one correspondence between the two species being coupled. Other procedures, such as immunogen production, require multiple couplings between many haptens and the carrier protein. The ability to monitor and control the coupling reactions involved in these processes is extremely valuable.

Coupling agents can introduce a reagent compound such as a label into the coupled complex. Alternatively they can provide a site for further coupling, that is be bifunctional. They can be homobifunctional, that is having two identical active groups or two groups which react with identical functionalities. They also can be heterobifunctional so as to react with one functionality on one species and with a different functionality on a second species. Typical homobifunctional agents employed heretofore include bis-isocyanates, bis-imidoesters, bis-diazotized benzidine, glutaraldehyde, bis-anhydrides, diphenyl azides, dimaleimides, and active diesters with carbamyl or thiocarbamyl groups, including the nitrogen and thio analogs thereof, as described in U.S. Pat. Nos. 4,334,069; 4,323,647; and 4,046,636. These agents have disadvantages because they cause intramolecular cross-linking and self-condensation.

Esters of N-hydroxysuccinimide are commonly used as heterobifunctional coupling agents. Examples of these materials include the m-maleimidobenzoyl-N-hydroxysuccinimide ester, as described in U.S. Pat. Nos. 4,253,996 and 4,214,048 and by T. Kitagawa, et al., *J Biochem* 79:233–236 (1976); the N-(4-carboxycyclohexylmethyl)maleimido-N-hydroxysuccinimide ester, as described by S. Yoshitake, et al., *Eur J Biochem* 101:395–399 (1979); and the iodoacetyl-N-hydroxysuccinimide ester, as described by E. Rector, et al., *J. Immunol Methods* 24:321–336 (1978). An additional reagent of this type is N-succinimidyl-3-(2-pyridyldithio) propionate as described by J. Carlsson, et al., *Biochem J* 173:725–737 (1978) and D. Pain, et al., *J Immunol Methods* 40:219–230 (1981). These prior agents are at best only sparingly soluble in water. In use, they must be dissolved in organic solvents, generally dimethylformamide, and this solution is then added slowly to aqueous solutions containing the species to be coupled. Under such conditions, control of the final concentration of the coupling agent, and thus of the rate and extent of reaction, is quite difficult. Because of this lack of control over the reaction, even when a coupling reaction is successful, it is typically very difficult to reproduce. Moreover, high concentrations of the organic solvent can interfere with the properties of many biologically important materials. For example such solvents can denature or precipitate out proteins.

In an attempt to improve the solubility of the esters, sulfo-N-hydroxysuccinimide esters have been used as coupling agents. While these esters do exhibit improved solubility in water, they do not lend themselves to processes where monitoring and close control are called for. This is because their leaving groups have low extinction coefficients and the wavelength at which their maximum absorbance occurs is 259 nm, which is close to the 280 nm wavelength region in which most proteins exhibit their maximum absorbance. Therefore, monitorability of the coupling reaction by measuring the absorbance of the detached leaving groups is poor because the proteins establish a high background against which only large changes can be detected. Such conditions do not allow one to detect, for example, one-to-one coupling between immunodiagnostic enzymes and antibodies.

Several o-nitro-p-sulfonic acid-phenyl esters (i.e. esters of 4-hydroxy-3-nitrobenzene sulfonic acid) have been described as coupling agents for amino acids. These materials are highly water soluble. For example, Klausner, et al., in *Peptides, Proceedings of the Fifth American Peptide Symposium*, ed. by M. Goodman, et al. (New York: John Wiley and Sons, 1977), p. 536–538, discloses synthesis of peptides in water using 4-hydroxy-3-nitro-benzene sulfonic acid sodium salt (HNSA) esters of N-protected amino acids. Gershkovich, et al., in *Bioorganicheskaya Khimiya* 4:1129 (1978), *Bioorganicheskaya Khimiya* 5:1125 (1979) and *Bioorganicheskaya Khimiya* 8:1486–1489 (1982) have similar teachings.

P. Bhatnagar, et al., in *Peptides:Synthesis-Structure-Function*, ed. by D. Rich, et al., (Rockford: Pierce Chemical Company, 1981), pp. 97–100, discloses that the N-2,4-dinitrophenyl-6-aminocaproic acid ester of HNSA is more efficient than the same ester of N-hydroxysuccinimide in conjugating to bovine serum albumin at pH 8.5. In addition, cells treated with biotin-HNSA exhibited a much larger increase in fluorescence than cells treated with biotin-p-nitrophenyl ester, when both were reacted with fluoresceinated avidin.

A special problem which comes up when the coupling involves proteins and peptides as the amine-containing material being coupled is the poor yields obtained. Gershkovich, et al., in *Bioorganicheskaya Khimiya* 5:1125 (1979) teaches that the rate of aminolysis by glycine (which contains only an alpha-amino group) at pH 7.4 using N-benzyloxycarbonyl-gly-HNSA (Z-gly-HNSA) ester is considerably higher than its hydrolysis rate. However, one of the most favored sites on a protein for chemical modification is not the α-amino group, but rather the ε-amino group of lysines because these latter groups are normally on the surface of the protein structure. The ε-amino group is also favored because there is usually a plurality of ε-amino groups but only one α-amino group on a protein or on a protein chain; thus, modification of ε-amino sites enables multiple functionalization of any given protein. The $pK_a$ of α-amines is lower than the $pK_a$ of ε-amine groups of lysine. The $pK_a$ of these latter groups ranges between 8.0 and 10.5 for most proteins, and only the deprotonated amine is sufficiently nucleophilic to attack active esters. Therefore, modification of protein amino groups with esters is normally performed at high pH's—e.g., 8.5, to deprotonate the amine. At such elevated pH's the high concentration of hydroxide ion results in extensive hydrolysis of the ester. This unwanted side reaction generally competes very favorably with the desired amide-forming reaction.

Accordingly, there is a need in the biochemical field for a coupling agent which is not only soluble in water but also can be precisely monitored to control the extent of the coupling reaction and, at the proper pH conditions, will result in high yields of the desired amide product.

SUMMARY OF THE INVENTION

The present invention satisfies the above-described criteria by providing a family of new water-soluble ester coupling agents and a process for their use. The process is especially suited for adding coupling agents to amine group containing materials and especially biological materials such as proteins and peptides, which process is precisely monitorable and thus controllable. The monitoring is effected by measuring the absorbance of a group release by the coupling agent which strongly absorbs at a wavelength far removed from the 280 nm spectral region at which the absorbance of most proteins interferes. In addition, the coupling product yields are often increased using the described process as compared to processes described heretofore.

More specifically, the present invention provides a process for precisely monitoring and controlling the coupling of an amine-containing material such as a biological material containing a free amine group to a reagent or the like using an activated ester coupling agent. This process comprises (a) reacting a 4-hydroxyl-3-nitrobenzene sulfonic acid sodium salt (HNSA) with a carboxylic acid moiety of a reagent compound to form an activated HNSA ester with the reagent compound; (b) reacting the ester with the amine-containing material, while (c) monitoring the progress of the reaction by measuring the absorbance of the reaction mixture at between about 350 nm and about 500 nm and especially at about 406 nm; and (d) terminating the reaction when the desired extent of reaction has occurred. Preferably, the amine-containing material has one or more ε-amino groups as its amine functionality. When the coupling agent has a reagent group that includes a second coupling functionality, a second reaction (e) may be carried out to provide coupling to a second material, typically a sulfhydryl-containing material.

An advantage of this process is that the reactions can, if desired, be carried out in an aqueous medium. This is made possible by the water solubility imparted by the sulfonic acid on the nitrophenyl ring.

The following scheme (Scheme I) illustrates an example of the coupling agents and a preferred embodiment of the present process in which an activated HNSA ester coupling agent (N-maleimido-6-aminocaproyl-HNSA, "mal-sac-HNSA") is formed and reacted with a protein through an ε-amino group on the protein and the resulting product is then coupled to the sulfhydryl moiety of a peptide: The subscripts "y" and "z" in Scheme I indicate the number of maleimido or maleimido-coupled peptide substituents attached to the individual protein molecules.

In another embodiment, an improved cross-linking process is provided for coupling material containing an ε-amino group, typically a biological material such as a protein, peptide or polypeptide to another, second material, typically containing a sulfhydryl moiety, wherein (a) the ε-amino group of the protein, peptide or polypeptide is reacted at a pH between about 5.5 and 10 and preferably between about 7.0 and 7.5 with a coupling agent comprising a 4-hydroxyl-3-nitrobenzene sulfonic acid sodium salt ester of a reagent compound containing a moiety reactive with the second material: (b) the resulting conjugate is separated from the reaction medium; and (c) the conjugate is then further reacted with the second material.

This invention also provides a family of new water-soluble ester coupling agents having the general formula:

In this structure will be the residue of a reagent compound (as that term will be defined herein) following release of the HNSA.

The present process offers many advantages over processes employed in the past for conjugation. Not only are the esters herein water soluble, but they also allow for precise monitoring of their coupling reaction. The monitoring of the uv absorption peak (e.g. 406 nm) of the HNSA dianion as it is released during coupling allows one to stop the reaction at any time, thus enabling precise control over the extent of conjugation. Furthermore, the undesirable ester hydrolysis reaction which competes with aminolysis in many coupling reactions proceeds at a rate lower than the rate of aminolysis in the pH range used herein of about 5.5 to 10.0 and especially pH's of from about 7.0 to about 7.5. The aminolysis reaction for ε-amino groups is still favored in this pH range, in which, furthermore, most proteins are stable as well.

DETAILED DESCRIPTION OF THE PREFERRED EMBODIMENTS

Definitions

As used herein, the following terms have the following meanings:

"Biological material" refers to compounds other than amino acids which contain amine groups that are free to react with the activated HNSA ester, e.g., mal-sac-HNSA, to form an amide linkage. Preferred biological materials contain one or more ε-amino groups. Examples of biological materials include carrier proteins such as bovine serum albumin, key-hole limpet hemocyanin (KLH), ovalbumin, enzymes, toxins, amine-containing lipid vesicles, polypeptides, cells, virus particles, chromatographic matrices and other materials. The biological material is preferably a protein, peptide or polypeptide which contains an ε-amino group. It should be noted that a biological material can be a naturally occurring material or can be of synthetic origin, as desired, e.g., poly(lysine) or synthetic polypeptides or the like.

"Amine-containing material" or "amine-group-containing material" as used herein includes all the biological materials and in addition polyamines including amine-containing polymers such as poly(ethyleneimine), poly(vinylamine) and the like, aminated chromatographic supports such as aminated sepharose, aminated silica gel and the like, and amine-containing membranes such as aminated nylon or aminated plastics such as poly(styrene).

"Material", "other material" or "another material" as used herein refer not only to amine-containing materials as defined above but also to reactive materials which contain reactive carboxyl, hydroxyl or sulfhydryl groups. Thus, the term "materials" includes insoluble matrices such as chromatographic materials, derivatized polysaccharides, silica gel derivatives, and the like, which contain any of the various functional groups. In addition, the term includes inert materials such as polystyrene beads that have been derivatized to contain various functional groups or which contain C—H bonds into which a "universal hook" enabling further functionalization can be inserted via free radical photochemcial initiation (e.g., a benzoylbenzoic moiety). Biological materials can be linked to these materials via the coupling agents herein to form cross-linked proteins or peptides, immunotoxins, immobilized insoluble antibodies, or chromatographic absorbents.

As noted above, and as illustrated by Scheme I, the activated esters which serve as coupling agents herein are typically initially reacted with an amine functionality of the "biological material" and subsequently with a sulfhydryl or other functionality of a "material", thus providing cross-linking between the two.

"Reagent compound" as used herein refers to one of at least six classes of compounds which contain either: (1) a carboxylic acid moiety inherently present in their structure for reaction with the 4-hydroxyl group of the HNSA to form an activated ester; or (2) a carboxylic acid moiety which has been attached to a reactive moiety present in their structure before the reaction with HNSA. Examples of the latter type of compound include certain steroids and poly(ethylene glycol) which have been reacted, e.g., with succinic anhydride, before reaction with the HNSA. Examples of classes of reagent compounds containing the carboxylic acid moiety include the following.

(1) A compound which contains a label that may be detected directly or a label that may be detected indirectly via a reaction which forms a detectable product, such as enzymes which are reacted with substrate to form a product which may be detected spectrophotometrically. Suitable direct label moieties include spectroscopic or photochemical labels such as fluorescent labels, e.g., fluorescein and rhodamine, chemiluminescent labels such as luciferin, radioactive isotopic labels such as $^{125}$I, $^{32}$P, $^{14}$C or $^{3}$H detectable by radioactive means, spin labels, bacteriophage labels, and the like. Suitable indirect labels are molecules recognizable by compounds which may in turn be detected, e.g., biotin, which is recognizable by avidin or streptavidin.

(2) A hapten, as defined in the *Dictionary of Microbiology* by P. Singleton, et al., (New York: John Wiley & Sons, 1978). Thus, the term "hapten" as used herein refers to a substance which elicits antibody formation only when combined with other molecules or particles (carriers), as compared to proteins which are themselves antigenic. Examples of haptens for purposes herein include peptides, drug derivatives, vitamins, antibiotics, hormones, adrenalin, steroids, and other compounds which when conjugated to a carrier protein, peptide or polypeptide will form an immunogen.

(3) A compound which in addition to a carboxylic acid moiety contains a group capable of reacting with another material, which reaction does not result in a directly observable signal, e.g., maleimido, bromoacetyl, and iodoacetyl.

(4) A compound which in addition to a carboxylic acid moiety contains an —SH group capable of reacting either with another —SH group on another material to give a disulfide linkage or with a maleimido or bromoacetyl moiety on another material to give a thioamine linkage.

(5) A compound of formula ω-S-S-X where X is a group which will give rise to an XS⁻ leaving group such as the unsubstituted or nitro-substituted 2-thiopyridyl group of Ellman's reagent and where "ω-S⁻" contains a carboxylic acid moiety and is capable of reacting with an —SH moiety on another material to yield a reducible disulfide bridge. The leaving group XS⁻ is preferably selected so that coupling to a material can be monitored by absorbance spectroscopy: X thus preferably includes an aromatic moiety as will be described.

(6) A compound containing benzophenone, which upon photoactivation acts as a "universal hook" by inserting into C—H bonds of organic surfaces such as polystyrene, polypropylene, etc., and allows for further functionalization. Such a compound can, for example, conjugate an antibody to an inert support such as a polystyrene bead.

The reagent compound is thus a precursor, along with HNSA, to the activated esters of the present invention. The "activated" HNSA esters which are the subject of the present invention are formed from reaction of HNSA with the carboxylic acid moiety of the reagent compound as defined above (see, e.g., Scheme I, which shows the condensation of HNSA with dicyclohexylcarbodiimide to give the activated ester mal-sac-HNSA).

In a preferred aspect of the invention, the activated esters have the formula:

and are formed by the reaction of HNSA with the reagent compound R—Y—COOH. In these preferred materials, R is typically a substituent selected from the group consisting of:

where Q is halogen and XS⁻ is a leaving group, X being typically of the structure where $R^1$ and $R^2$ are independently selected from the group consisting of hydrogen, $NO_2$ and COOH. In a preferred embodiment, X is selected from the group consisting of Y is a divalent covalent spacer moiety. Y is selected to provide separation between the carbonyl-containing HNSA ester present at one end of the coupling agent and the active functionality supplied by or bonded to the reagent compound at the other end of the coupling agent. It is common to observe that close proximity between the coupled moieties (for example an antibody and a labeling enzyme) is deleterious and that increased separation is advantageous.

In selecting Y spacer groups, it is generally desirable to avoid groups which will interact significantly in a physical, chemical or immunological sense with the moieties present within the active ester or with other compounds in the environment of use. Typically, since the coupling agent is usually used in an aqueous medium, the spacer units should not react with the aqueous medium and should not be unduly hydrophobic. If the spacer has substantial hydrophobic regions, they may bind to hydrophobic regions of the materials being coupled and coprecipitate.

With these general considerations in mind, the spacer may be selected from cyclic or acyclic aliphatic hydrocarbon spacer moieties.

Examples of cyclic aliphatic hydrocarbon Y spacers include cyclohexyl-1,4-ene, cyclopentyl-1,3-ene and the like with or without alkyl substituents. Typical cyclic aliphatic spacers have from 5 to 8 carbon atoms in their cyclic ring with from 0 to 3 carbons in substituents depending from the ring. Cyclohexyl-1,4-ene is a preferred cyclic aliphatic spacer.

Typical acyclic aliphatic hydrocarbon Y spacers can be branched or straight chain. They can contain from 1 to about 10 chain carbons. Preferred acyclic aliphatic spacers contain from about 2 to about 8 carbon atoms in the spacer chain and are saturated. Examples of acyclic aliphatic spacers include ethylene, propylene, butylene, 2,4-dimethylbutylene, pentylene, 2-methylpentylene, n-hexylene, decylene and the like.

Another group of useful spacers include oxygen-containing divalent units. The oxygens can be present as hydroxyls or as ether oxygens. Hydroxyls or ethers tend to decrease hydrophobicity and increase the hydrophilic character of the spacer. They are also advantageous for the very practical reason that a number of such materials are available commercially.

Typical oxygen-containing spacers include poly(vinyl alcohol)-, poly(ethylene glycol)-, poly(propylene glycol)-based materials, i.e., polymers having the units respectively (and copolymers of these units) where n is a number from about 1 to about 100, and especially from about 2 to about 50.

The spacers can also include an additional functionality which can be used to join the spacer to the carboxyl which forms the HNSA ester on the one end and to the R group on the other end. This additional functionality can include amines, which are reacted with an anhydride such as succinic anhydride or glutaric anhydride or the like to provide the HNSA-linking carboxyl and with bromoacetyl halide, bromoacetyl-sac, mal-sac or the like to provide the R group or link to the R group.

Representative oxygen-containing spacers include the poly(ethylene glycol) ether and poly(propylene glycol) ether materials set forth above, the amine-terminated ether oligomer 4,9-dioxa-1,12-di-aminodecane. $NH_2$—$(CH_2)_3$—O—$(CH_2)_4$—O—$(CH_2)_3$—$NH_2$— and the poly(oxyalkyleneamine)s such as the Jeffamines sold by Texaco Chemical Co.

Poly(oxyalkylamine) materials are generally formed from ethylene and/or propylene oxide and thus have the general structure where r is hydrogen, in the case of ethylene oxide-based materials and r is $CH_3$ in the case of propylene oxide based materials. Commercially available materials have values for n ranging from about 2 to 35 or higher. Other equivalent spacers can be used as well without departing from the sense of this invention.

When incorporated in the coupling agents, the terminal amine groups are generally present as amide links as previously described.

The reagent compound defined above by R—Y—COOH may contain an R moiety that can react with a hapten, an enzyme or other polypeptide, a label, e.g., a radioactive or fluorescent species, or with a specific group designed for attachment of another material (e.g., biotin).

The R groups set forth above are all specifically reactive with sulfhydryl moieties to give either —C—S—, —NH—S—S— or —S—S— linkages.

The group of compounds where R is —S—S—X could replace and improve upon a cross-linking reagent, SPDP, sold by Pharmacia, of the formula:

which suffers from lack of water solubility, virtually impossible quantitation and poor monitoring at the N-hyroxysuccinimide reaction step of the material with the ester. In contrast, the HNSA esters herein are water soluble and readily monitorable during reaction of the material with the ester. The compounds where X is a label moiety detectable quantitatively such as are especially preferred for cross-linking reactions because they allow both the initial and the subsequent coupling reactions to be monitored, i.e., first by release of the HNSA dianion at one end of the molecule and second by release of the XS⁻ leaving group at the other end of the molecule. This is especially useful, for example in preparing toxin antibody conjugates for cancer therapy.

The preferred of these novel esters are those where R is

-continued or and Y is a $-(CH_2)_n$ acyclic alkylene radical where n is an integer from 2 to 10 inclusive.

Preparative Methods

The HNSA esters described above may all be prepared by the following basic procedure wherein 4-hydroxy-3-nitrobenzene sulfonic acid sodium salt (HNSA) is reacted with a reagent compound containing the carboxylic acid moiety to form an ester. The procedure involves reacting together approximately molar equivalents of the reagent compound, HNSA, and a dehydrating agent, e.g., carbodiimide, under ambient conditions in an organic solvent which will solubilize all of the reactants, preferably a polar solvent such as dimethylformamide (DMF). One skilled in the art will readily recognize the reaction as a conventional condensation reaction between a hydroxyl moiety and a carboxylic acid to give an ester. The following scheme illustrates a typical embodiment of the reaction:

The carboxylic acid moieties employed in this reaction (i.e., the reagent compound or R—Y—COOH) are commercially available or may be readily synthesized according to standard methods known in the art.

Where Y contains a diamine spacers, e.g., $NH_2$—$(CH_2)_3$—O—$(CH_2)_4$—O—$(CH_2)_3$—$NH_2$, for example, the reagent compound R—Y—COOH is prepared by first converting one of the amine moieties to a carboxylic acid moiety by reaction with an anhydride (preferably succinic anhydride or glutaric anhydride), while the other amine moiety is then caused to react with "R" (see Examples 10 and 11 and *Peptides: Synthesis—Structure—Function*, Ed. Rich et al., Rockford, Ill.: Pierce Chemical Co., 1981). The dehydrating agents employed in this reaction are preferably the well-known carbodiimides. They may be symmetrical or asymmetrical. Synthesis of HNSA esters in general is described by Bhatnagar, et al., supra, and reference may be had thereto for further information relating to the details of relevant synthetic procedures.

The HNSA esters prepared as described above are directly soluble in water without the need for intervening organic solvents. Thus, they can, be readily dissolved in, for example, phosphate buffers at final concentrations of about 1.0M. This dissolving is essentially instantaneous. In addition to aqueous solubility and monitorability upon release, the esters herein have the added advantage of not causing substantial loss of biological activity or significant denaturation of the biological materials to which they are linked.

After the ester is prepared it can be used as a crude preparation or it can be purified if desired, e.g., by chromatographic means, to remove contaminating HNSA, unreacted carboxylic acid moiety, urea product of carbodiimide, etc. The free HNSA contaminant does not interfere with the coupling but can provide a "background" which can reduce the sensitivity of measurements of "released" HNSA. Maximum monitoring sensitivity is facilitated by utilizing HNSA ester of purity equal to or greater than 50% with respect to HNSA contamination (i.e., 50% or less HNSA) and especially 80% or greater purity. The purified esters are generally labile to hydrolysis under high temperatures and in the presence of bases and nucleophiles. However, they can be stored as a dry powder indefinitely at room temperature if stored with a desiccant, or in an anhydrous form at temperatures about 0° C. or less, or as a frozen aqueous solution for at least six months.

Coupling of the activated ester proceeds as follows. The ester is reacted with the material which is chosen for conjugation, preferably a biological material having a free amine moiety. This reaction proceeds concurrently with the release of the free HNSA dianion, as illustrated in Scheme I above, and below in Scheme II, which shows the coupling of bovine serum albumin to mal-sac-HNSA. This reaction may be carried out generally at temperatures ranging from about 4° C. to about 30° C., depending on the material and ester selected. Typically the reaction takes place in an aqueous medium buffered to a pH between about 5.5 and 10.0, preferably between about 6.5 and 8.0, depending again on the specific ester and material employed. For example, the pH is preferably kept to below about 7.0 if the ester contains a maleimido group, but may rise to 8.5 or higher for esters bearing iodoacetyl or bromoacetyl groups. The reaction is most preferably carried out within a pH range selected so that the rate of aminolysis is greater than the rate of the competing, unfavorable ester hydrolysis reaction. The pH employed will also depend on the the type of buffer used. Conventional buffer systems such as phosphate buffered saline (PBS) or similar systems which do not contain nucleophiles (e.g., amines or mercaptans) that would compete for the amino or sulfhydryl groups on the biological materials are ideal for the conjugation reactions.

Figure 1:
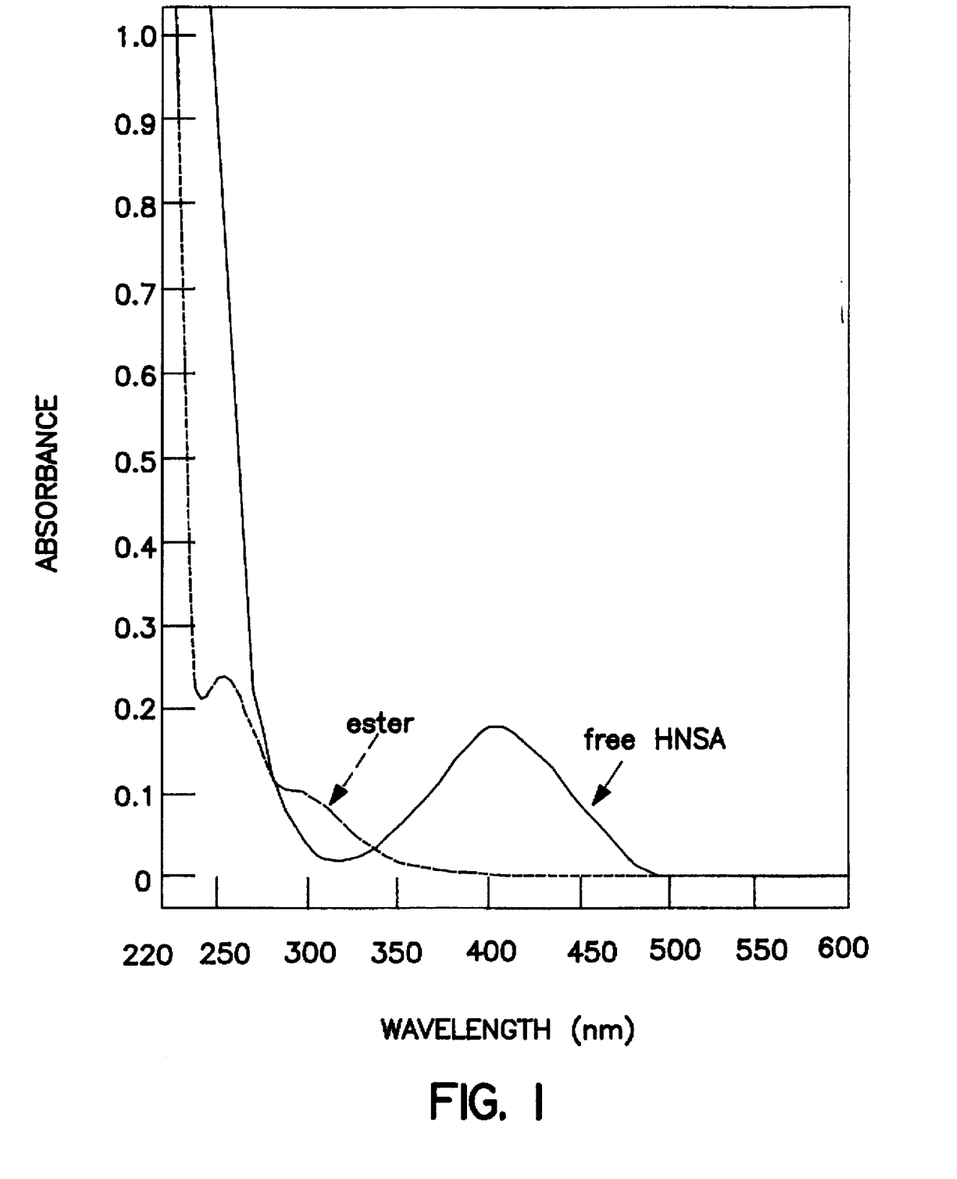
FIG. 1 depicts the absorption spectrum of an HNSA ester before and after hydrolysis with sodium hydroxide, showing the peak appearing at about 406 nm after hydrolysis of the ester.

As noted above, a primary advantage of the invention is that the reaction between ester and material can be monitored by measuring the absorbance of the reaction mixture, during coupling, at between about 350 and 500 nm, preferably between about 375 and 425 nm and especially at about 406 nm (see FIG. 1). Pure esters of HNSA formed from typical organic acids show virtually no absorbance in the spectral region above 300 nm. Upon reaction with nucleophiles such as amino or hydroxyl moieties, however, the HNSA dianion which is released as a leaving group absorbs strongly between about 350 and 500 nm, a region far removed from the 280 nm region at which most proteins and peptides absorb. FIG. 1 illustrates the difference between the absorbance of N-maleimido-6- aminocaproyl-HNSA (mal-sac-HNSA) ester before and after treatment with the nucleophile NaOH. The results show that the absorbance band between about 350 and 500 nm, peaking at about 406 nm, is prominent in the spectrum of the free HNSA dianion after treatment with NaOH.

In the typical procedure for reaction of the activated ester with a biological material, for purposes of illustration an amine-containing protein, the protein is dissolved in a phosphate buffer adjusted to a pH within the aforementioned range. The activity of active ester, whether in a crude preparation, or after storage, is assayed as follows. The ester is rapidly dissolved in a small amount, preferably 1 ml or less (i.e., selected so as to effect solution), of distilled water, and a small aliquot of this solution is diluted into 10 mM phosphate buffer, pH in the aforementioned ranges, preferably approximately 7.0. The two solutions are admixed and the absorbance of the diluted aliquot at about 406 nm is then measured, recorded, and used to calculate the initial concentration of free HNSA dianion (if any) present prior to reaction. Using the extinction coefficient for free HNSA dianion of $4.6 \times 10^3$ liters/mole-cm, the concentration of HNSA dianion may be calculated via Beer's law from the measured absorbance.

To the diluted aliquot of HNSA ester may be then added a concentrated base such as NaOH, which rapidly hydrolyzes the ester to component acid and HNSA dianion, thereby increasing the absorbance which peaks at 406 nm. A new HNSA dianion concentration is calculated, and the difference between that concentration and the initial concentration represents the actual concentration of active ester. Knowing this concentration and the concentration of amine groups in the material, one can readily calculate the amount of ester needed to be added to the solution of material to achieve the desired degree of substitution (represented by "y" in Scheme I). Thus, in contrast to prior art methods, it is now possible by way of the present method to carefully control the amount of ester which is reacted with the protein. For example, using N-hydroxy-succinimide esters and a mixed organic/aqueous phase, one would know the amount of ester added to the organic solvent but not the amount of ester which actually dissolved into the water or the amount which may have been hydrolyzed.

Figure 2:
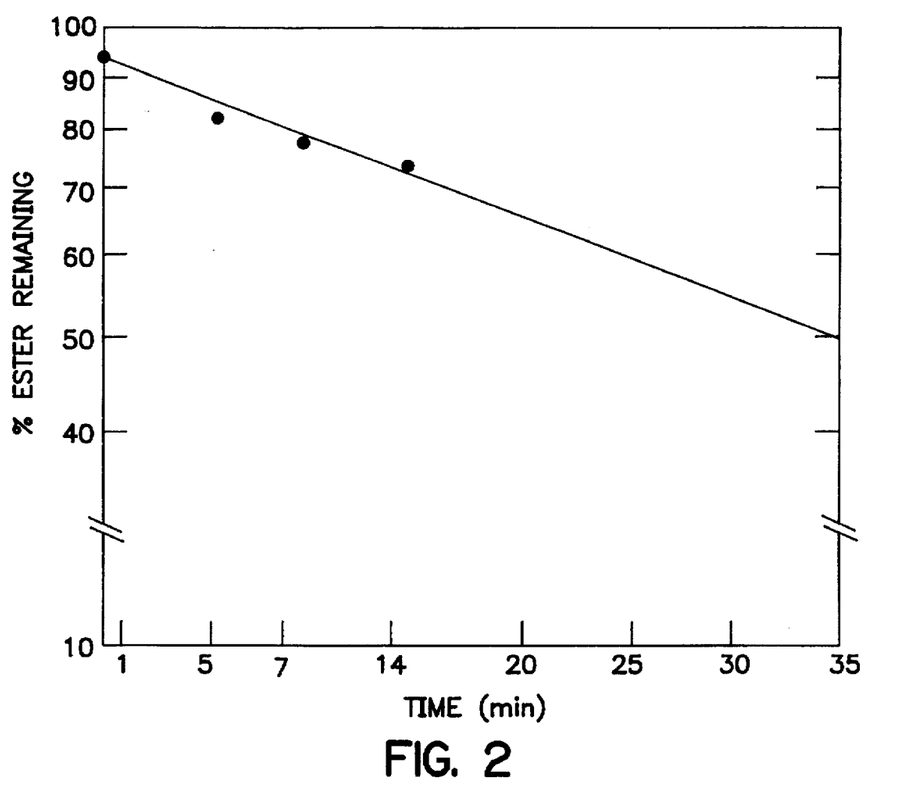
FIG. 2 is a plot of the progress of reaction of bovine serum albumin with mal-sac-HNSA ester as a function of time, as determined by monitoring the percent ester remaining in the reaction mixture.

The calculated amount of ester is then added to the solution of material and mixed. Aliquots of the mixture may be removed at reasonable time intervals (e.g., every 5 minutes) and tested as above both for the amount of HNSA dianion produced as well as for the amount of free ester remaining. This procedure allows one to follow precisely the extent of the reaction. FIG. 2 shows a plot of the percent of reaction between bovine serum albumin (BSA) and malsac-HNSA (described more fully in Example 2) as a function of time using this monitoring procedure. The reaction is as follows:

Scheme II

The capability of accurately monitoring the extent and rate of reaction is quite important, as it enables one to stop the reaction at any desired degree of coupling. Not all proteins have precisely predictable $pK_a$ values for their ε-amino moieties, and steric hindrance inherent in some protein structures may influence the reaction to an unknown extent. In the process herein, the reaction can be stopped when the desired degree of modification has occurred by, for example, lowering the pH to below about 5.5 or removing the modified biological material from the reaction mixture using, e.g., a gel chromatographic column equilibrated with phosphate buffer. (The pH is preferably about 6.0. ) Thus, the invention provides not only a means for monitoring the rate of reaction but also a means for controlling the precise degree of modification effected.

The coupling technique described above is useful in a number of applications. For example, the process can be used to prepare immunogens, whether for production of polyclonal or monoclonal antibodies, by coupling haptens covalently to protein carriers or natural or synthetic polypeptide carriers. One problem in producing reproducible antibodies has been the difficulty in synthesizing a carrier with the optimum number of haptens, a difficulty characterized in the past by guesswork and imprecision. The process of the present invention alleviates this problem by precisely controlling the degree of coupling. In one form of preparation of such immunogens, the HNSA is first reacted with the carboxylic acid moiety of a hapten. Suitable haptens herein include, for example, those containing a carboxyl group such as the drug derivative acetylsalicylic acid, and those to which a carboxyl moiety can be attached, such as morphine, digoxin, and certain steroids.

After esterification of the hapten moiety to the HNSA, the resulting ester may be reacted with a natural or synthetic carrier protein or polypeptide. The protein carriers which may be employed for this purpose are derived from various sources. Specific examples of these include bovine serum albumin, key-hole limpet hemocyanin, ovalbumin, bovine-gamma-globulins, thyroglobulins, etc. Preferably, the carrier protein is bovine serum albumin or key-hole limpet hemocyanin. Preferred synthetic polypeptide carriers are polymers containing lysine.

With these immunogens, anti-hapten antibody specificity is advantageously directed at the part of the hapten molecule farthest away from the functional group by which it is linked to the protein or polypeptide carrier. For example, highly specific antibodies may be raised to conjugates where the attachment to a steroid is via a spacer joining the carrier protein to a position on the steroid molecule which is not important for its biological specificity—e.g., the C-6 position of an estrogen, or the C-6 or C-11 position of progesterone. Therefore, using esters with longer spacer arms such as $(CH_2)_x$ chains between the hapten moiety and HNSA ester linkage may result in producing immunogens which raise antibodies more specific to the hapten.

As discussed above, the conjugate of HNSA ester and the amine-containing material may be further reacted in a second, cross-linking step, with a second material, which may or may not be a biological material. For this second reaction to occur, the R moiety of the complex formed by reaction of active ester with the amine-containing material where β represents the amine-containing biological material, is preferably selected from the group consisting of:

where Q and X are as earlier-defined. Each of these R moieties, as noted above, is reactive with a sulfhydryl functionality. Thus, this second reaction typically couples β-COYR to a sulfhydryl-containing compound by a disulfide or other type of linkage. That is, upon coupling to a second material γ, the cross-linked product will be given by R may be selected so as to react with other types of functionalities, depending on the material to be coupled. For example, bovine serum albumin contains several types of available reactive functional groups: the ε-amino groups of lysine residues, the phenolic groups of tyrosine residues, the sulfhydryl groups of cysteine residues, and the imidazole groups of histidine residues. The type of reactive group to be employed in preparing the HNSA ester ab initio will be determined by the desired two materials to be employed, taking into consideration its relative reactivity with the various functional groups of the materials. For example, a biotin moiety on the HNSA ester can bind noncovalently with avidin, while the N-maleimido, bromoacetyl , and iodoacetyl moieties will yield nonreducible thioether bonds when reacted with the sulfhydryl moieties on the first material employed.

The conditions employed for the second, cross-linking, reaction will depend on the particular reagents employed but frequently are the same as those described for the first reaction—i.e., a pH of about 5.5 to 10.0, preferably 6.5 to 8.0, and a reaction temperature of about 4°–30° C. Generally the conditions are the same as those described for known conjugation and/or cross-linking reactions. It may be necessary to introduce a sulfhydryl moiety on the second material prior to reaction. This can be accomplished, depending on the type of material, by reducing an existing disulfide. If the protein or chromatographic material does not contain a disulfide, a sulfhydryl moiety may be introduced by first reacting amine groups with S-acetyl-mercapto succinic anhydride, then removing the acetyl group from the sulfur. This reaction is generally run at temperatures below 20° C., preferably about 4° C., for periods of up to about 20 hours. All excess reagents are preferably removed either by gel filtration or by dialysis.

The second reaction may be monitored if the reactive moiety attached to the first reaction product is detectable as a leaving group. For example, if the product contains a —S—S—X moiety reactive with an —SH moiety in the second material and the product contains a detectable leaving group, XS⁻ then the second coupling reaction can be monitored throughout its course by detecting the increasing presence of the leaving group. As a particular example, if X is the corresponding leaving group can be detected by measuring the absorption at about 398 nm so that the second reaction may be precisely monitored and controlled until the desired extent of reaction has occurred, at which point the reaction can then be terminated.

One example of an application where the reaction product of the first coupling is cross-linked to a second material is in preparing immunotoxins for therapeutic use. Using the dual conjugation process herein, an antibody, preferably a monoclonal antibody with tumor cell specificity, is conjugated with precise monitoring to an HNSA ester of a reagent compound containing a moiety reactive with a functional group on the cytotoxic moiety. In the second reaction, the conjugated antibody is reacted with the cytotoxic molecule to prepare an antibody-cytotoxic agent conjugate directed against the antigen. The present process enables improvement in the control and reproducibility of the reaction used to prepare immunotoxins.

Examples of suitable antibodies for this purpose include those directed against breast cancer, prostate cancer, colon cancer, lung cancer, and other carcinomic or pathogenic antigens. The antibodies may be monoclonal antibodies produced by hybridomas or may be appropriate polyclonal antibodies.

Examples of cytotoxic moieties which may be reacted with the antibody-ester conjugate include cytotoxic drugs, enzymatically active toxins of bacterial or plant origin, and enzymatically active fragments ("A chains") of such toxins. Examples of enzymatically active toxins and fragments thereof include diphtheria A chain, exotoxin A chain (from *Pseudomonas aeruginosa*), ricin A chain, abrin A chain, modeccin A chain, alpha-sarcin, *Phytolacca americana* proteins (PAP I, PAP II and PAP-S), methotrexate, etc.

The process herein may also be used in diagnostic applications. Thus, antibodies as described above may be conjugated to label moieties providing that the reagent compound coupled to HNSA contains a label moiety. For example, a detectable enzyme, chemiluminescent, or fluorescent label may be linked to a hapten, antigen, antibody or binding analog thereof using the heterobifunctional HNSA esters herein to form conjugates useful in specific binding assays. The HNSA esters herein may be used, for example, to conjugate biotin to antibodies for use in an assay to detect CEA or Hepatitis B or to couple an enzyme with avidin. Homogeneous enzyme immunoassays require that the binding of the labeled hapten to the corresponding antibody induce a detectable modification in the specific activity of the enzyme. The factors to consider in choosing the enzyme and hapten to prepare such a conjugate are the location of the covalent bond on the hapten molecule (which may influence antigenic specificity and eventual cross-reactions), the optimum size of the spacer arm on the ester linking the enzyme to the hapten, the nature of the chemical reacting group of the enzyme which will accept the hapten, and the optimum number of hapten molecules to be covalently coupled on one molecule of enzyme. The latter factor will in turn depend on the conditions of the coupling reaction. Ratios of hapten to enzyme may vary from 1:1 to 30:1 or more.

The HNSA esters herein may also be used to conjugate antigens or haptens to carriers to be used in producing antibodies for use in immunoassays, as described in U.S. Pat. Nos. 4,235,969 and 4,230,805.

In summary, in the instant invention, the HNSA ester is so designed to be used in an aqueous rather than organic solvent, thereby facilitating solubility and precise monitoring of the reaction. Also, using the HNSA ester herein allows for better control over the hapten-enzyme ratio ultimately obtained.

The examples which follow further illustrate the invention. In the examples all parts and percentages are by weight unless otherwise noted and all temperatures are in degrees Celsius.

EXAMPLE 1

A. Preparation of mal-sac-HNSA Ester

One molar equivalent (2.24 g) of 4-hydroxy-3-nitrobenzene sulfonic acid sodium salt (HNSA) was mixed together with one molar equivalent (2.06 g) of dicyclohexylcarbodiimide and one molar equivalent (2.10 g) of N-maleimido-6-aminocaproic acid in 25 ml of dimethylformamide (DMF) at room temperature overnight. A white precipitate of dicyclohexylurea was formed. The precipitate was filtered and 300 ml diethyl ether was added to the mother liquor. After about 10 minutes to 4 hours a gummy solid precipitated from the mother liquor. This solid was found to contain 58% of active HNSA ester and 42% of free HNSA.

The analysis consisted of dissolving a small amount of the precipitate in 10 mmolar phosphate buffer at pH 7.0 and measuring absorbance at 406 nm; this reading provides the amount of unreacted free HNSA which is the contaminating material in the crude HNSA ester. Addition of very small amounts of concentrated strong base (5N NaOH) hydrolyzed the ester. A second reading was taken. Subtraction of the first reading from the second yielded the amount of ester in the original material. For purification purposes, the solid was dissolved in DMF, placed on a LH20 Sephadex column and eluted with DMF so that the ester was separated from the contaminating free HNSA. The progress of purification was monitored by thin layer chromatography using chloroform, acetone, and acetic acid (6:3:1 vol/vol) as eluting solvent. The product was positively identified as mal-sac HNSA ester by its reactivity with amines. The yield of crude ester produced was estimated to be approximately 30% of theoretical; the purified material consisted of 99% ester.

The ester thus obtained was found to dissolve fully in water and was found to be stable in water for several hours, provided no nucleophiles were added. The purified ester was found to be stable for extended periods when stored desiccated.

B. Preparation of Biotin-HNSA Ester

One molar equivalent (1.97 g) of HNSA was mixed together with one molar equivalent (1.85 g) of dicyclohexylcarbodiimide and one molar equivalent (2.0 g) of biotin in 50 ml of dimethylsulfoxide at room temperature overnight. The reaction resulted in the formation of dicyclohexyl urea as a precipitate. The precipitate was filtered off and 400 ml of dichloromethane was added to the mother liquor. After several hours a solid precipitate was formed. The yield of this crude ester was 59% of theoretical. This precipitate was analyzed spectroscopically as described in Example IA and found to contain 38% biotin-HNSA ester together with 68% of free HNSA. The solid was then purified by column chromatography on LH20 Sephadex in DMF and positively identified as described above for the preparation of mal-sac HNSA ester. The purification yielded biotin-HNSA ester of greater than 99% purity.

The ester thus obtained was found to have essentially the same physical properties as those described above for the mal-sac HNSA ester.

C. Preparation of 3-(2-pyridyldithio)propionyl-HNSA Ester

One molar equivalent (1.63 g) of HNSA was mixed together with one molar equivalent (1.4 g) of dicyclohexylcarbodiimide and one molar equivalent (1.45 g) of 3-(2-pyridyldithio)propionic acid in 70 ml of DMF at room temperature for 16 hours. A white dicyclohexyl urea precipitate appeared after a few minutes. The precipitate was filtered and the mother liquor was concentrated in vacuo to a small volume (about 10 ml). Diethyl ether, 300 ml, was added to this concentrated solution. A yellow oil precipitated from solution upon the addition of the diethyl ether; it solidified in 2 hrs. The precipitate was collected by filtration and gave a yield of 1.97 g of crude product. The solid was analyzed as described above and found to contain 45% 3-(2-pyridyldithio)propionyl-HNSA ester together with 55% HNSA. The solid was then purified and positively identified as described above for the preparation of mal-sac HNSA ester. The resulting ester was found to have essentially the same properties as those described above for the mal-sac HNSA ester.

EXAMPLE 2

A. Analysis of mal-sac HNSA Ester

About 0.5 mg of the purified mal-sac HNSA ester from Example 1A was dissolved in 1 ml of distilled water. A 10 µl aliquot of this solution was diluted into 1 ml of 10 mM phosphate buffer at pH 7.0. The absorbance at 406 nm was used to calculate the concentration of free HNSA as described in Example 1A. When 50 µl of 4.8N sodium hydroxide solution was added to the diluted aliquot of ester and mixed, the absorbance of the solution at 406 nm increased significantly, indicating that the hydroxide nucleophile rapidly hydrolyzed the ester to component acid and free HNSA dianion.

The difference between the post-base and initial free HNSA concentration represents the concentration of ester. From the actual concentration of ester the amount of ester to be added to the protein solution to achieve the desired degree of substitution can be calculated. The absorbance spectra of the two ester solutions with and without base are shown in FIG. 1.

B. Preparation of Conjugate of mal-sac-HNSA Ester and Bovine Serum Albumin (BSA)

A total of 22 mg (20 µmoles) of BSA (of molecular weight 66,296) was dissolved in 2.0 ml of 0.01M phosphate buffer at pH 7.5 to yield a total amino concentration of $1.0 \times 10^{-2}$ moles per liter (assuming 59 lysines/BSA molecule). A calculated amount (11 mg, $2.35 \times 10^{-5}$ moles) of the mal-sac HNSA ester (97.7% pure) of Example 1A in powder form was dissolved in 2.0 ml of the BSA solution. The reaction was carried out at room temperature. Ten µl aliquots were removed from the solution at timed intervals and were each diluted into 1.0 ml of 0.01M phosphate buffer at pH 7.0. The spectrum of each diluted aliquot was recorded using a Hewlett-Packard spectrophotometer and the absorbance at 406 nm measured. A total of 50 µl of 4.8N NaOH was then added to each aliquot, each aliquot was mixed and its spectrum retaken and the absorbance at 406 nm measured. The results appear in Table 1.

TABLE 1

| Time (minutes) | Without NaOH | | With NaOH | | | |
|---|---|---|---|---|---|---|
| | Absorbance Peak at 406 nm | Concentration of HNSA (moles/l) | Absorbance Peak at 406 nm | Concentration of HNSA (moles/l) | Concentration of Ester (moles/l) | Percent Ester Remaining in Solution |
| 0 | 0.046 | $1.03 \times 10^{-5}$ | 0.648 | $1.66 \times 10^{-4}$ | $1.56 \times 10^{-4}$ | 94.0 |
| 5 | 0.095 | $2.44 \times 10^{-5}$ | 0.547 | $1.40 \times 10^{-4}$ | $1.16 \times 10^{-4}$ | 82.9 |
| 9 | 0.112 | $2.87 \times 10^{-5}$ | 0.516 | $1.32 \times 10^{-4}$ | $1.03 \times 10^{-4}$ | 78.3 |
| 14 | 0.147 | $3.77 \times 10^{-5}$ | 0.579 | $1.49 \times 10^{-4}$ | $1.11 \times 10^{-4}$ | 74.5 |

From the absorbance at 406 nm before and after addition of base the concentration of ester remaining and the percent ester reacted were determined for the reaction mixtures. The percent of ester is plotted as a function of time in FIG. 2, and the results show that the reaction rate is essentially linear over a 15 minute period.

It was found at 15 minutes of reaction time that $2.6 \times 10^{-3}$ moles/l of the ester had reacted and thus 25.9% of the 59 ε-amino groups of BSA were presumably substituted. Thus, the product contained 16 mal-sac groups per molecule. After 15 minutes the reaction was stopped by applying the reaction mixture to a PD10 desalting Sephadex G-25 column (Pharmacia, Inc.) equilibrated with 0.1M phosphate buffer at pH 6.0.

C. Preparation of Immunogen

The product of the first reaction (mal-sac-BSA) was isolated by applying the reaction mixture to a PD10 desalting Sephadex G-25 column equilibrated with 0.1M phosphate buffer at pH 6.0. The Sephadex column separates large molecules (conjugated BSA) from small molecules (free HNSA, remaining mal-sac-HNSA, hydrolyzed mal-sac free acid, etc.) The protein peak is not retained on the column and comes out first. The column was eluted with 0.1M phosphate buffer in 1.0 ml fractions. The column solution was followed by monitoring the absorbance spectrum and peak fractions containing the mal-sac-BSA were pooled. 18 mg of cysteine-containing tetradecapeptide, mol. wt. 1686, and the pooled mixture of BSA were mixed and stirred at room temperature overnight. Following extensive dialysis against distilled water and lyophilization, the product was purified by chromatography through a Sephadex G-25 column equilibrated in 0.01N ammonia. The product, which eluted in the void volume, was pooled and lyophilized. Comparative amino acid analysis of starting BSA material and peptide-BSA conjugate showed that 8 peptide groups were attached to one BSA molecule; thus the yield (with respect to mal-sac substitution) was 50%.

EXAMPLE 3

Preparation of Conjugate of mal-sac- HNSA Ester and Avidin

An amide of mal-sac-HNSA ester and avidin was prepared as follows:

A total of 220 μl of an aqueous solution of 4.65 mg of avidin per ml of solution (27 amino groups per avidin molecule) was charged to a siliconized glass tube with a stir bar. Approximately 1.5 mg of the mal-sac HNSA ester of Example 1A (of 88.5% purity), calculated from the data of Example 2A, was added and the mixture stirred at room temperature. Ten μl aliquots of the mixture were removed and added to 1.0 ml of 10 mM phosphate buffer at pH 7.0 at timed intervals. The spectrum of each aliquot was taken and then 50 μl of 4.8N NaOH solution was added to each aliguot and the spectrum was retaken. The results are shown in Table 2.

TABLE 2

| Time (minutes) | Absorbance Peak at 406 nm | | Percent Ester Remaining |
|---|---|---|---|
| | Without NaOH | With HaOH | |
| 0 | 0.033 | 0.282 | 89 |
| 5 | 0.037 | 0.273 | 86 |
| 10 | 0.047 | 0.254 | 81 |
| 20 | 0.055 | 0.255 | 78 |
| 30 | 0.069 | 0.257 | 73 |

Figure 3:
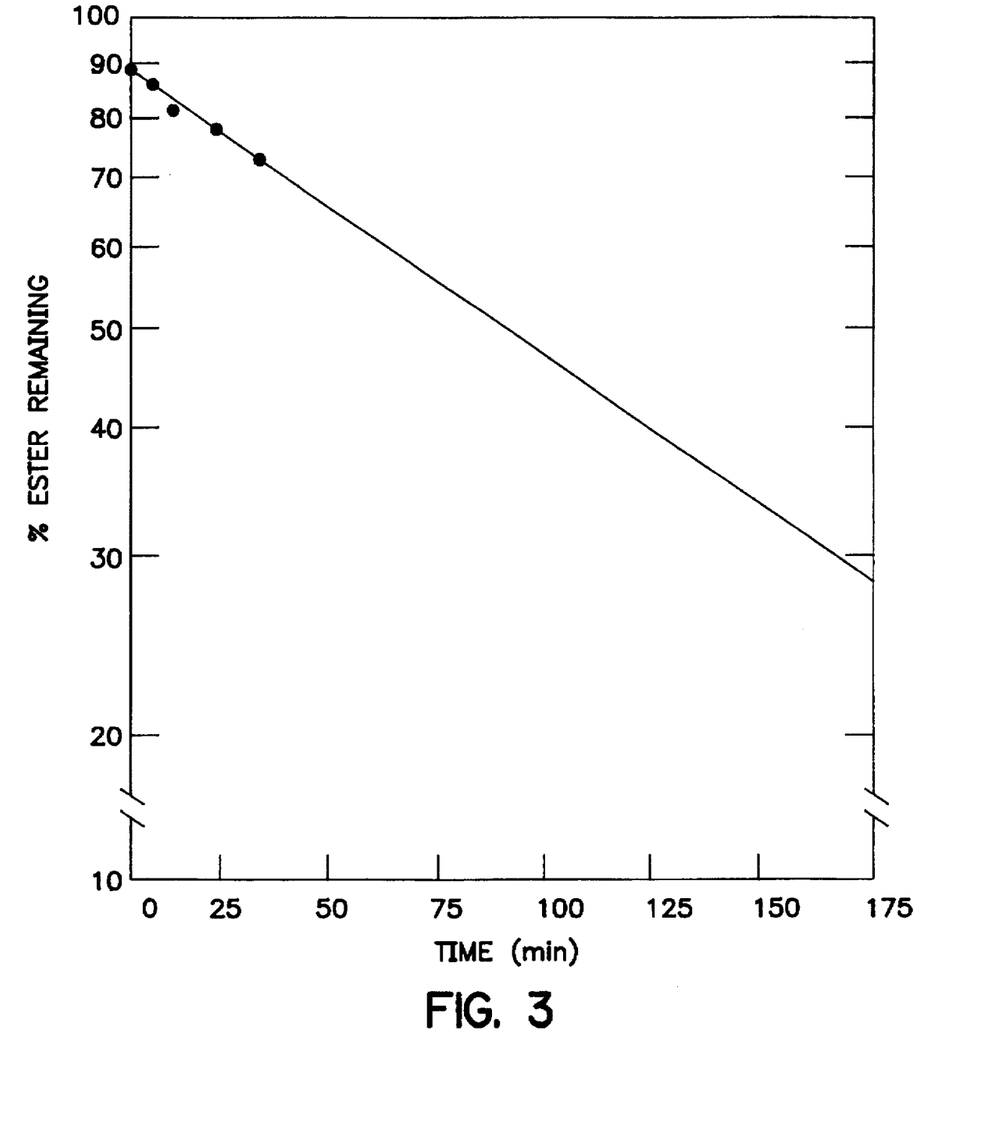
FIG. 3 is a plot of percent of ester remaining in the reaction mixture as a function of time when mal-sac-HNSA is conjugated to avidin.

The percent of ester is plotted as a function of time in FIG. 3, and the results show that the reaction rate is linear.

The number of amino groups of the avidin which reacted was calculated from the difference in absorbance of the reaction mixture at 406 nm at the end versus the beginning of the reaction divided by the extinction coefficient of free HNSA ($4.6 \times 10^3$ /mole-cm) to obtain the amount of HNSA released, which was used to determine that 13.5 amino groups reacted with the ester in 30 minutes.

After 30 minutes the reaction was terminated by applying the reaction mixture to a PD10 desalting Sephadex G-25 column (Pharmacia, Inc.) equilibrated with a pH 6.0 buffer consisting of 100 mM sodium phosphate and 2 mM EDTA. The column was eluted with the same buffer and collected in 12 (0.65 ml) fractions. The absorbance spectrum of each fraction was measured using the Hewlett-Packard spectrophotometer at 280 and 406 nm. The peak fraction was reacted by slowly dripping it into stirring horseradish peroxidase-SH which had been modified to introduce free —SH groups with 2-(acetylthio) succinic anhydride, then with hydroxylamine to remove acetyl groups from the sulfur. The mixture was allowed to react at room temperature for 1.5 hours.

The final product was separated on a Sephadex G-150 column and yielded a species of about 100,000 molecular weight which exhibited both the enzymatic activity of HRP and the biotin binding activity of avidin.

EXAMPLE 4

Preparation of Conjugate of mal-sac HNSA Ester and Streptavidin

An amide of mal-sac ester and streptavidin was prepared as follows:

A total of 0.26 mg ($4.3 \times 10^{-3}$ μmoles) of streptavidin purified from *Streptomyces avidinii* by the method of Hoffman et al., PNAS, 77, 4666–4668 (1980) was dissolved in 1.0 ml of phosphate buffered saline at pH 7.4 to yield a total amine concentration of $6.93 \times 10^{-5}$M (16NH$_2$/streptavidin). Then, about 1 mg ($2 \times 10^{-6}$ moles) of the mal-sac HNSA ester of Example 1A, calculated from the data in Example 2A, was dissolved in 1.0 ml of the streptavidin solution. The mixture was stirred at room temperature to initiate reaction. Ten μl aliquots were removed from the incubating solution at timed intervals and were each diluted into 1.0 ml of 0.01M phosphate buffer at pH 7.0. The spectrum of each diluted aliquot was recorded and the absorbance at 406 nm measured. A total of 50 μl of 4.8N NaOH solution was then added to each aliguot, each aliquot was mixed and its spectrum retaken and the absorbance at 406 nm measured the results showed that the reaction rate was essentially linear over the period measured.

After 20 minutes the reaction was stopped using a Sephadex G-25 column as described in Example 2A. Fractions were collected and measured for absorbance at 406 nm and 280 nm. Good separation was achieved between the protein and the excess HNSA and unreacted HNSA ester. From the difference between the absorbances at 406 nm at the end of the reaction and at the beginning of the reaction, the moles of HNSA ester which reacted can be calculated. In this case 79% of the amino groups on streptavidin (12.9 out of 16.0) reacted.

EXAMPLE 5

Preparation of Conjugate of mal-sac HNSA Ester and Horseradish Peroxidase (HRP)

An amide of mal-sac HNSA ester and HRP was prepared as follows:

A total of 40 mg (1.0 μmoles) of HRP (Sigma Chemical Co.) was dissolved in 0.5 ml of 0.1M phosphate buffer at pH 7.0 to yield an amine concentration of $3.7 \times 10^{-3}$M. Then, 5 mg ($1.1 \times 10^{-5}$ moles) of the mal-sac HNSA ester of Example 1A, calculated from the data in Example 2A, was dissolved in 0.5 ml of the HRP solution. The mixture was stirred at room temperature. Five μl aliquots were removed from the incubating solution at timed intervals and were each diluted into 1.0 ml of 0.01M sodium phosphate buffer at pH 7.0. The spectrum of each diluted aliguot was recorded and the absorbance at 406 nm measured. A total of 50 μl of 4.8N NaOH was then added to each aliquot, each aliquot was mixed and its spectrum retaken and the absorbance at 406 nm measured. Because HRP has an absorbance at 406 nm due to its heme group and this absorbance changes after addition of sodium hydroxide, corrections for the absorbances due to the HRP were made on every dilution. The results showed that the reaction rate was essentially linear over a 30 minute period.

After 30 minutes the reaction was stopped using a Sephadex G-25 column as described in Example 2A. Fractions were collected and measured for absorbance at 406 nm and 280 nm. From the calculations it was determined that the product has 3 mal-sac groups per molecule.

EXAMPLE 6

A. Preparation of Conjugate of Biotin HNSA Ester and Polylysine

An amide of biotin HNSA ester and polylysine was prepared as follows:

A total of 25 mg (0.34 μmoles) of polylysine obtained from Sigma Chemical Co. (Sigma) was succinylated to approximately 20 amines remaining unsuccinylated per polylysine molecule, and redissolved in 0.5 ml of 0.1M phosphate buffer at pH 7.4 to yield an amine concentration of $1.0 \times 10^{-2}$M. Five mg ($1.0 \times 10^{-5}$ moles) of the biotin HNSA ester was dissolved in 0.5 ml of the polylysine solution. The mixture was stirred at room temperature to initiate reaction. Ten μl aliquots were removed from the incubating solution at timed intervals and were each diluted into 1.0 ml of 0.01M phosphate buffer at pH 7.0. The spectrum of each diluted aliquot was measured and the absorbance at 406 nm recorded. The percent ester remaining was calculated as in Example 1A. The results showed that the reaction rate was essentially linear over a 5 minute period.

After 7 minutes the reaction was stopped using a Sephadex G-25 column as described in Example 2A. From the calculations it was determined that 28% of the amino groups of the polylysine polypeptide reacted. Thus, the product has 4.2 biotin groups per molecule.

B. Preparation of a Conjugate of mal-sac-HNSA Ester with Biotinylated Polylysine, then Attachment to HRP-SH to form Biotinylated Polylysine-HRP The biotinylated polylysine collected from the Sephadex G-25 column in 0.1M phosphate buffer, pH 6, was reacted with mal-sac-HNSA as follows:

Biotinylated polylysine (0.6 ml; 73,000 D average mol. wt.) was adjusted to pH 7.4 with 0.015 ml of 2.5N NaOH. Approximately 5 mg of mal-sac-HNSA was added to the biotinylated polylysine and stirred at room temperature. Ten μl aliquots were removed from the mixture at timed intervals and diluted into 1.0 ml of 0.01M phosphate buffer at pH 7.0. The spectrum of each diluted aliquot was measured and the absorbance at 406 nm recorded. A total of 50 μl of 4.8N NaOH solution was then added to each aliquot, mixed, and the spectrum retaken. The percent ester remaining was calculated as described in Example 1A.

The reaction rate was essentially linear over a 30 minute period. Calculations indicated that 18 mal-sac groups were covalently attached per polylysine molecules. After 30 minutes of incubation time, the reaction was stopped using a Sephadex G-25 column, and the high molecular weight (biotin)$_4$-polylysine-(sac-mal)$_{18}$ was well separated from excess HNSA and unreacted mal-sac-HNSA. 0.5 ml of the above was added slowly to 2.0 ml of HRP-SH in 0.1M phosphate buffer (pH 6.0, 5 mM EDTA) and allowed to stir overnight in the cold room. The biotin-polylysine-sac-mal-S-HRP was separated from free HRP-SH on a Sephacryl-300 column. The high molecular weight conjugate eluted with an apparent size of 400,000 D, which is consistent with the base polymer of approximately 73,000 D and approximately 8 HRP molecules of molecular weight 40,000 D apiece.

EXAMPLE 7

Determination of Hydrolysis and Aminolysis rates of the Biotin- HNSA Ester

Figure 4:
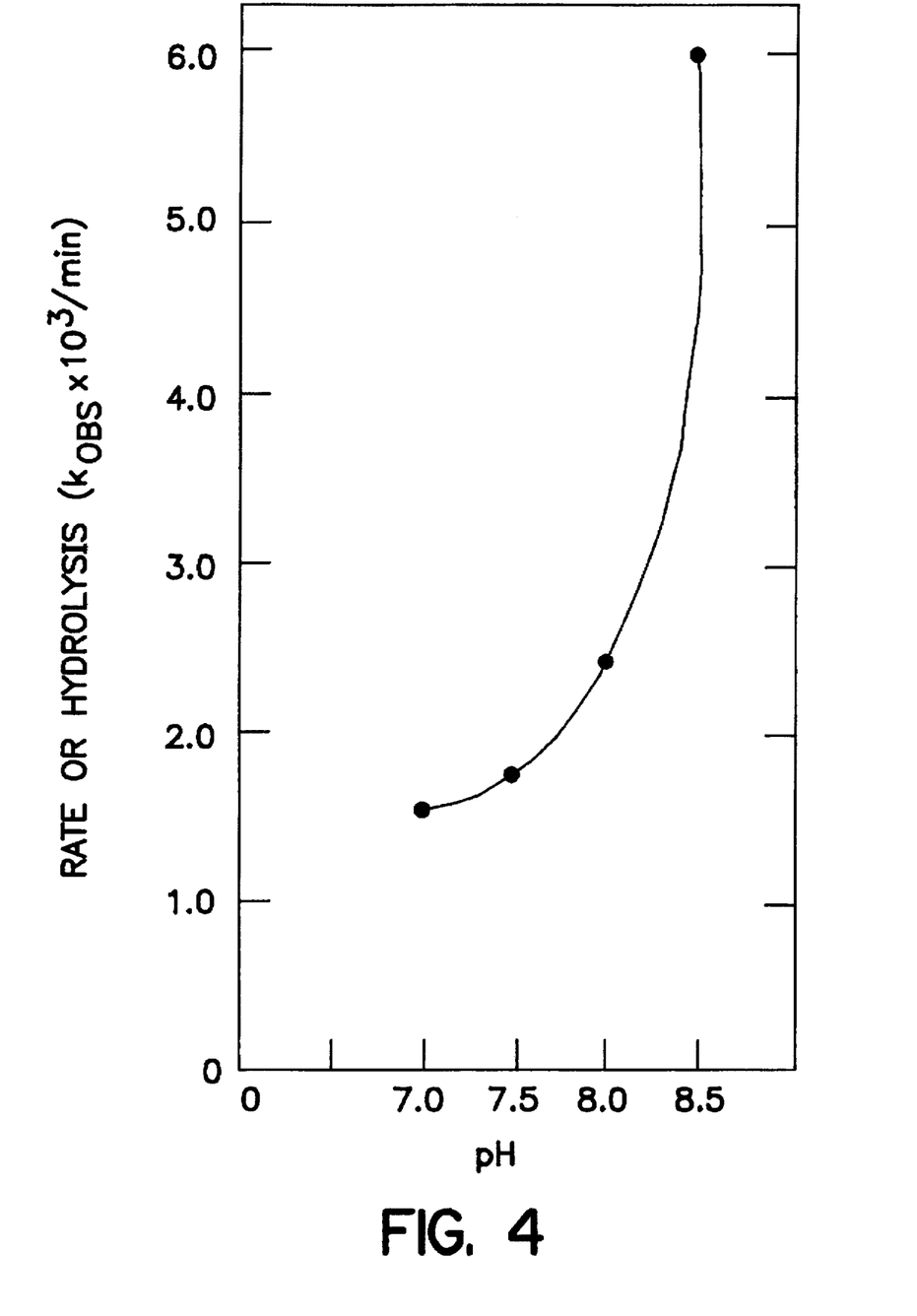
FIG. 4 is a plot of the rate of hydrolysis of biotin-HNSA ester as a function of pH.

The hydrolysis and aminolysis rates of the biotin-HNSA ester were determined as a function of pH, with Nα-acetyl-L-lysine methyl ester hydrochloride as the amine so that only the ε-amine of the lysine was free to react. At pH 8.5 and 8.0, 0.1M bicine buffer (N,N-bis(2-hydroxyethyl) glycine) which does not contain a primary amine was used for hydrolysis and aminolysis. At pH 7.5 and 7.0, 0.1M sodium phosphate buffer was used. The reaction mixtures contained 1.0M NaCl, 0.1M buffer and 2×10$^{-4}$ biotin-HNSA ester for hydrolysis and concentrations of the acetyl-lysine ranging from 0.1 to 5×10$^{-4}$M for aminolysis. The increase in absorbance at 406 mn was followed at discrete time intervals using a programmable spectrophotometer. The hydrolysis rate as a function of pH is shown in FIG. 4.

EXAMPLE 8

Use of Dansyl-sac-HNSA Ester to Label Sheep Red BLood Cells

Dansyl-sac-HNSA ester was prepared as described in Example 1A using molar equivalents of HNSA, dicyclohexylcarbodiimide and dansyl-ε-aminocaproic acid (from Sigma Chemicals). For use in coupling to sheep red blood cells (SRBC) the dansyl-sag-HNSA ester (50 mg) was prepared in 7 ml of 0.28M cacodylate buffer, pH 6.9.

Sheep red blood cells were washed 4 times (400×g, 8 minutes) in G-PBS buffer (5% α-D-glucose w/v in PBSCa-Mg). To 1 ml of packed red blood cells was added the 7 ml of dansyl-sac-HNSA ester dropwise with gentle mixing for 10 minutes at room temperature. The reaction was done in foil-wrapped glassware to protect against photodecomposition. Following the reaction the cells were washed in cold G-PBS buffer containing 1% heat inactivated (56° C., 30 minutes) FCS (fetal calf serum) until the supernatants were colorless (a minimum of 4 washes).

The dansyl-sac-HNSA labelled SRBC were monitored using a Coulter EPICS V Cytofluorometer immediately after labeling and at 24 hours. The labelled cells showed an emission maximum between 475 and 515 nm upon excitation at 360 nm. This translates to an increase in intensity 720 times over unlabeled cells.

EXAMPLE 9

Synthesis of 4-Benzoyl-Benzoic Acid-HNSA Ester 2.42 g HNSA (10 mmoles) was dissolved in 10 ml DMF to which was added 2.26 g 4-benzoyl-benzoic acid (10 mmoles) and 2.06 g dicyclohexylcarbodiimide (10 mmoles). Almost immediately, the dicyclohexyl urea formed in the reaction began to precipitate. After 4 hours, the solution was filtered and the dicyclohexyl urea precipitate was discarded. To the mother liquor was added approximately 200 ml of dry ethyl ether. The solution was left at room temperature overnight during which a precipitate formed. The precipitate was collected by filtration and washed with dry ether. Thin layer chromatography analysis on silica gel plates showed the presence of 4-benzoyl-benzoic acid-HNSA ester and free unreacted HNSA, but no unreacted 4-benzoyl-benzoic acid. Using this procedure 3.2 g of crude ester was obtained. The yield of crude ester was, therefore, 71% of theoretical. Spectral analysis showed this material to contain 32% 4-benzoyl-benzoic acid-HNSA ester and 68% of free HNSA. Purification on an LH-20 Sephadex column in DMF resulted in a product of 98% purity.

EXAMPLE 10

Synthesis of "Maleimide-Spacer HNSA"

In this example, the following activated ester was prepared:

In the following description, "mal" represents maleimide, "mal-sac" represents N-maleimido-6-aminocaproic acid, "glut" represents glutaryl group, "spacer" represents

—NH—(CH$_2$)$_3$O(CH$_2$)$_4$O(CH$_2$)$_3$—NH— and "boc" is tertiary butyloxycarbonyl, a commonly used protecting group in peptide synthesis. The strategy adopted here was: (1) prepare "mono-boc-spacer"; (2) react mono-boc-spacer with glutaric anhydride to give boc-spacer-glut; (3) remove the protecting group to yield H$_2$N-spacer-glut ; (4) react mal-sac-HNSA with H$_2$N-spacer-glut to yield mal-sac-NH-spacer-glut-COOH; and (5) activate the latter product with HNSA to give the compound defined by the above structure.

"Boc-spacer" was prepared by reaction of 4,9-dioxa-1, 12-dodecanediamine (Aldrich) with 2-(tert-butyloxy-carbonyloxyamino)-2-phenyl-acetonitrile ("Boc-ON", Aldrich) in methanol and was purified by extraction and preparative low-pressure chromatography in silica gel. 4.10g (13.5 mmole) of the resultant "boc-spacer" compound was dissolved in 40 ml pyridine (Baker, lot 207091) with stirring. Glutaric anhydride (Aldrich; 3.08 g; 27 mmole) was added to the stirring solution and allowed to react overnight. On the following day, the solvent was removed by extraction and the residue was dissolved in methylene chloride. The mixture was washed three times with 0.5M citric acid (H$_2$O) in a separating funnel, then washed three times with saturated NaCl (H$_2$O) three times. The methylene chloride layer was dried with anhydrous MgSO$_4$ and stripped to a thick oil. The material was purified and its identity confirmed using 90:10 CHCl$_3$:HOAc (the authentic compound was noted to run halfway up analytical TLC using that solvent system; most impurities are less polar and elute before boc-spacer-glut).

The "boc" protecting group was then removed as follows. Boc-spacer-glut (1.48 g: 3.54 mmole) was dissolved in 20 ml trifluroacetic acid and stirred for about one hour at room temperature. The solvent was removed by vacuum distillation. The remaining TFA salt of HN-spacer-glut was dissolved in 6 ml dimethylformamide and titrated to a pH of about 8 with diisopropylethylamine to deprotonate the amine.

To the H₂N-spacer-glut solution in DMF was added 2 g maleimido-6-aminocaproyl-HNSA (4.6 mmole) as prepared in Example 1. The solution was stirred at room temperature and monitored by diluting 2 μl aliquots to 5.0 ml with 0.01M sodium phosphate. In order to monitor release of the free HNSA dianion upon coupling, the absorbance at 406 nm, $A_{406}$, was read, 50 μl NaOH was added, and $A_{406}$ was reread several times. The results were plotted (percent ester remaining versus time) and the amount of ester reacted determined therefrom—at 35 min. —to be equivalent to 0.904 g of the H₂N-spacer-glut. The mal-sac-spacer-glut was separated from smaller molecules on an LH20 Sephadex column (Pharmacia; 4.5 cm in diameter by 40 cm) in DMF. Fractions which eluted first were pooled and solvent was removed with high vacuum.

The mal-sac-spacer-glut was further purified by silica gel chromatography using 90:10:10 CHCl₃:HOAc:MeOH. Positive fractions were pooled and solvent was removed by rotary evaporation.

Activation of mal-sac-spacer-glut with HNSA:

Synthesis of bromoacetyl-6-aminocaproic acid:

Aminocaproic acid (Sigma; 65.6 g; 0.5 mole) and potassium hydroxide (0.5 mole) were dissolved in 150 ml water cooled in an ice-acetone bath. Bromoacetyl bromide (Fluke; 52 ml; 0.6 mole) was added in five portions, five minutes apart, with rapid stirring. After each addition of bromoacetyl bromide, 50 ml K₂CO₃ (2.8N in H₂O) was added. The final pH was 7.8.

The complete reaction mixture was stirred for one hour at −10° C., and the pH was then adjusted to about 3 with 12N aqueous HCl. The water solution was extracted three times with 500 ml ethyl acetate.

The mal-sac-spacer-glut prepared in the previous step (0.53 g; 1 mmole) was dissolved in 4 ml DMF. A total of 480 mg HNSA (11 mmole) and 400 mg dicyclohexyl-carbodiimide (2.3 mmole) were added, and the reaction mixture was stirred overnight.

The resulting mal-sac-spacer-glut-HNSA given by the above structure was separated from other materials on an LH-20 Sephadex column (Pharmacia) in DMF. Larger fractions were pooled and the solvent was stripped by vacuum. The identity of the product was confirmed by its ability to cross-link monoclonal antibody and ricin toxin HA in a similar fashion as its analog, mal-sac- HNSA, described in Example 1.

The combined EtOAc extracts were washed with 500 ml H₂O, dried over anhydrous Na₂SO₄ and evaporated to an oily residue under vacuum. The unreacted aminocaproic acid was removed on a Sil acid. Dicyclohexylurea could be seen to begin precipitating. After 4 hours of reaction at room temperature, dicyclohexyl urea was removed by filtration and diethyl ether was added to mother liquor to precipitate the product. The product was triturated with ether and the solid was recovered by filtration. The solid was assayed using the difference in absorbance at 406 nm as described above to determine that crude product contained about 65.4% of the ester.

In summary, the present invention is seen to provide a coupling agent which allows precise monitoring and controlling of reactions to couple materials.

Other modifications of the above described embodiments of the invention that are obvious to those of skill in the area of chemistry, biochemistry and related disciplines are intended to be within the scope of the following claims.

We claim:

1. A method for conjugating an activated ester to an amine-containing biological material β, comprising:

dissolving the amine-containing biological material β in a buffered solution adjusted to a pH of about 5.5 to 10.0, thereby providing a first solution;

providing a second buffered solution having a pH of about 5.5 to 10.0, an activated ester of formula:

wherein Y is a divalent covalent spacer moiety and R is selected from the group consisting of:

wherein Q is halogen and X is selected from the group consisting of wherein $R^1$ and $R^2$ are independently selected from the group consisting of H, $NO_2$ and COOH; and admixing the first and second solutions, whereupon reaction of the amine-containing biological material with the activated ester gives the coupled product while releasing a dianion and;

measuring the amount of released dianion spectroscopically at a wavelength from about 350 to about 500 nm to monitor and control conjugating of the activated ester to the amine-containing biological material.

2. The method of claim 1, wherein the wavelength is from about 375 to about 425 nm.

3. The method of claim 1, wherein said coupling is effected at a pH of from about 6.5 to 8.

4. The method of claim 1, wherein the biological material is a protein, peptide or polypeptide.

5. The method of claim 1, wherein the biological material is a protein.

6. The method of claim 5, wherein the protein is bovine serum albumin or key-hole limpet hemocyanin.

7. The method of claim 1, additionally comprising the step of further coupling the coupled product at the R substituent with a sulfhydryl group of a second material to give 8. The method of claim 7, wherein the further coupling is a spectroscopically monitorable reaction.

9. The method of claim 7, wherein the further coupling is carried out in a phosphate buffer having a pH in the range of 5.5 and 10.0.

10. The method of claim 9, wherein the pH is in the range of 6.5 and 8.0.

11. The method of claim 7, wherein the amine-containing biological material is a toxin and the second material is an antibody.

* * * * *